(12) United States Patent
Fukuda

(10) Patent No.: US 11,587,215 B2
(45) Date of Patent: Feb. 21, 2023

(54) IMAGE PROCESSING DEVICE, IMAGE PROCESSING METHOD, IMAGE PROCESSING PROGRAM, IMAGE DISPLAY DEVICE, IMAGE DISPLAY METHOD, AND IMAGE DISPLAY PROGRAM

(71) Applicant: FUJIFILM Corporation, Tokyo (JP)

(72) Inventor: Wataru Fukuda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 82 days.

(21) Appl. No.: 17/002,716

(22) Filed: Aug. 25, 2020

(65) Prior Publication Data

US 2021/0082095 A1 Mar. 18, 2021

(30) Foreign Application Priority Data

Sep. 17, 2019 (JP) .............................. JP2019-168506

(51) Int. Cl.
  *G06T 5/50* (2006.01)
  *A61B 6/02* (2006.01)
  (Continued)

(52) U.S. Cl.
  CPC ................ *G06T 5/50* (2013.01); *A61B 6/025* (2013.01); *G06T 7/0016* (2013.01);
  (Continued)

(58) Field of Classification Search
  CPC ....... G06T 5/50; G06T 7/0016; G06T 11/006; G06T 2207/10116; G06T 2207/30168;
  (Continued)

(56) References Cited

U.S. PATENT DOCUMENTS 6,611,575 B1 8/2003 Alyassin et al.
8,983,156 B2 3/2015 Periaswamy et al.
(Continued)

FOREIGN PATENT DOCUMENTS

JP   H07194598 A  *  8/1995
JP   2006-130223 A    5/2006
(Continued)

OTHER PUBLICATIONS

The extended European search report issued by the European Patent Office dated Feb. 8, 2021, which corresponds to European Patent Application No. 20196187.7-1126 and is related to U.S. Appl. No. 17/002,716.
(Continued)

*Primary Examiner* — Jeffery A Brier
(74) *Attorney, Agent, or Firm* — Studebaker & Brackett PC

(57) ABSTRACT

A combination unit generates a plurality of composite two-dimensional images from a plurality of tomographic images acquired by performing tomosynthesis imaging on an object using different generation methods. In this case, the combination unit generates a first composite two-dimensional image having a quality corresponding to a two-dimensional image acquired by simple imaging or a second composite two-dimensional image in which a structure included in the object has been highlighted as at least one of the plurality of composite two-dimensional images.

5 Claims, 11 Drawing Sheets

(51) Int. Cl.
  *G06T 7/00* (2017.01)
  *G06T 11/00* (2006.01)

(52) U.S. Cl.
  CPC ... *G06T 11/006* (2013.01); *G06T 2207/10116* (2013.01); *G06T 2207/30068* (2013.01); *G06T 2207/30168* (2013.01); *G06T 2210/41* (2013.01); *G06T 2211/421* (2013.01)

(58) Field of Classification Search
  CPC ....... G06T 2210/41; G06T 2207/30068; G06T 2211/421; A61B 6/025; A61B 6/5235; A61B 6/502; A61B 6/463
  See application file for complete search history.

(56) References Cited

U.S. PATENT DOCUMENTS

| | | | |
|---|---|---|---|
| 9,792,703 B2 | 10/2017 | Costa et al. | |
| 2008/0019581 A1* | 1/2008 | Gkanatsios | G06T 11/006 382/131 |
| 2009/0123052 A1* | 5/2009 | Ruth | A61B 6/025 382/132 |
| 2009/0141955 A1 | 6/2009 | Morita | |
| 2011/0109650 A1 | 5/2011 | Kreeger et al. | |
| 2012/0069951 A1 | 3/2012 | Toba | |
| 2013/0077749 A1* | 3/2013 | Akahori | A61B 6/584 378/62 |
| 2014/0015856 A1 | 1/2014 | Xiao et al. | |
| 2014/0093029 A1 | 4/2014 | Masumoto et al. | |
| 2014/0226783 A1 | 8/2014 | Ning et al. | |
| 2014/0327702 A1* | 11/2014 | Kreeger | G09G 5/377 382/131 |
| 2015/0131777 A1* | 5/2015 | Makifuchi | A61B 6/5217 378/36 |
| 2015/0356732 A1 | 12/2015 | Fukuda | |
| 2015/0379374 A1 | 12/2015 | Fukuda | |
| 2016/0051215 A1 | 2/2016 | Chen et al. | |
| 2016/0078621 A1* | 3/2016 | Nagae | A61B 6/507 382/130 |
| 2018/0055459 A1 | 3/2018 | Fukuda | |
| 2018/0109698 A1 | 4/2018 | Ramsay et al. | |
| 2018/0174341 A1 | 6/2018 | Palma et al. | |
| 2019/0059838 A1 | 2/2019 | Shimada | |
| 2019/0162679 A1 | 5/2019 | Yamakawa et al. | |
| 2020/0372693 A1 | 11/2020 | Kobayashi | |

FOREIGN PATENT DOCUMENTS

| | | | |
|---|---|---|---|
| JP | 2008-068032 A | 3/2008 | |
| JP | 2009136376 A | 6/2009 | |
| JP | 2012-061196 A | 3/2012 | |
| JP | 2014-014679 A | 1/2014 | |
| JP | 2014-68752 A | 4/2014 | |
| JP | 2014128716 A | 7/2014 | |
| JP | 2014-183876 A | 10/2014 | |
| JP | 2014-188250 A | 10/2014 | |
| JP | 2016-510669 A | 4/2016 | |
| JP | 2018029746 A | 3/2018 | |
| JP | 2019-037576 A | 3/2019 | |
| WO | WO-2012128031 A1 * | 9/2012 | ............. A61B 6/463 |

OTHER PUBLICATIONS

An Office Action mailed by the United States Patent and Trademark Office dated Mar. 28, 2022, which corresponds to U.S. Appl. No. 16/925,776 and is related to U.S. Appl. No. 17/002,716.

An Office Action; "Notice of Reasons for Refusal," mailed by the Japanese Patent Office dated Jun. 21, 2022, which corresponds to Japanese Patent Application No. 2019-138865 and is related to U.S. Appl. No. 17/002,716; with English language translation.

An Office Action mailed by the United States Patent and Trademark Office dated Aug. 8, 2022, issued in U.S. Appl. No. 16/925,776, which is related to U.S. Appl. No. 17/002,716.

An Office Action mailed by the Japanese Patent Office dated Jun. 7, 2022, which corresponds to Japanese Application No. 2019-168506 with English translation.

An Office Action; "Notice of Reasons for Refusal," mailed by the Japanese Patent Office dated Oct. 18, 2022, which corresponds to Japanese Patent Application No. 2019-138865; with English language translation.

An Office Action; "Notice of Reasons for Refusal," mailed by the Japanese Patent Office dated Oct. 4, 2022, which corresponds to Japanese Patent Application No. 2019-168506; with English language translation.

* cited by examiner

IMAGE PROCESSING DEVICE, IMAGE PROCESSING METHOD, IMAGE PROCESSING PROGRAM, IMAGE DISPLAY DEVICE, IMAGE DISPLAY METHOD, AND IMAGE DISPLAY PROGRAM

CROSS REFERENCE TO RELATED APPLICATIONS

The present application claims priority under 35 U.S.C. § 119 to Japanese Patent Application No. 2019-168506 filed on Sep. 17, 2019. The above application is hereby expressly incorporated by reference, in its entirety, into the present application.

BACKGROUND OF THE INVENTION

Technical Field

The present disclosure relates to an image processing device, an image processing method, and an image processing program that generate a composite two-dimensional image from a plurality of tomographic images acquired by tomosynthesis imaging and an image display device, an image display method, and an image display program that display the composite two-dimensional image.

Related Art

In recent years, image diagnosis using a radiography apparatus (called mammography) for capturing an image of the breast has attracted attention in order to promote early detection of breast cancer. Further, in the mammography, tomosynthesis imaging has been proposed which moves a radiation source, irradiates the breast with radiation from a plurality of radiation source positions to acquire a plurality of projection images, and adds the plurality of acquired projection images to generate tomographic images in which desired tomographic planes have been highlighted. In the tomosynthesis imaging, the radiation source is moved in parallel to a radiation detector or is moved so as to draw a circular or elliptical arc according to the characteristics of an imaging apparatus and the required tomographic image and imaging is performed on the breast at a plurality of radiation source positions to acquire a plurality of projection images. Then, the projection images are reconstructed using, for example, a back projection method, such as a simple back projection method or a filtered back projection method, or a sequential reconstruction method to generate tomographic images.

The tomographic images are generated in a plurality of tomographic planes of the breast, which makes it possible to separate structures that overlap each other in the depth direction in which the tomographic planes are arranged in the breast. Therefore, it is possible to find an abnormal part such as a lesion that has been difficult to detect in a two-dimensional image (hereinafter, referred to as a simple two-dimensional image) acquired by simple imaging according to the related art which irradiates an object with radiation in a predetermined direction.

In addition, a technique has been known which combines a plurality of tomographic images having different distances (positions in a height direction) from a detection surface of a radiation detector to a radiation source, which have been acquired by tomosynthesis imaging, using, for example, an addition method, an averaging method, a maximum intensity projection method, or a minimum intensity projection method to generate a pseudo two-dimensional image (hereinafter, referred to as a composite two-dimensional image) corresponding to the simple two-dimensional image (see JP2014-128716A). In the composite two-dimensional image, an abnormal part included in the tomographic image is less affected by the tissues in the thickness direction of the breast than that in the simple two-dimensional image. Therefore, the use of the composite two-dimensional image makes it easy to interpret an abnormal part in the breast with one image.

In contrast, in the medical field, a computer aided diagnosis (hereinafter, referred to as CAD) system has been known which automatically detects a structure, such as an abnormal shadow, in an image and displays the detected structure so as to be highlighted. For example, the CAD is used to detect important structures in diagnosis, such as calcifications, spicula, and tumor, from the tomographic images acquired by the tomosynthesis imaging. In addition, a method has been proposed which, in a case in which a composite two-dimensional image is generated from a plurality of tomographic images acquired by performing the tomosynthesis imaging on the breast, detects a region of interest including a structure using the CAD and combines the detected region of interest on, for example, a projection image or a two-dimensional image acquired by simple imaging to generate a composite two-dimensional image (see U.S. Pat. No. 8,983,156B). Further, a method has been proposed which combines tomographic images including only the structure detected by the CAD to generate a composite two-dimensional image (see U.S. Pat. No. 9,792,703B). The use of the methods described in U.S. Pat. Nos. 8,983,156B and 9,792,703B makes it possible to generate a composite two-dimensional image in which an abnormal shadow is easily observed since the structure, such as the abnormal shadow, is highlighted.

However, in the tomosynthesis imaging, in a case in which an object is irradiated with radiation, an incidence angle is limited to a certain range. Therefore, for example, in a case in which projection images are superimposed by the back projection method to reconstruct tomographic images, artifacts which are virtual images of the structures may appear in the tomographic images in the depth direction in which tomographic planes are arranged. Specifically, the back projection may cause an artifact to appear in a region, in which a structure does not originally exist, in a tomographic image of a tomographic plane that is different from the tomographic image of the tomographic plane in which a structure originally exists.

Therefore, a method has been proposed that reduces artifacts in the depth direction of the structure and generates a composite two-dimensional image which has a quality corresponding to a two-dimensional image acquired by simple imaging and in which information on the thickness of an object has been reflected (see JP2018-029746A). The method described in JP2018-029746A generates a plurality of band tomographic images indicating frequency components in each of a plurality of frequency bands for each of a plurality of tomographic planes of the breast which is an object on the basis of a plurality of projection images, projects the plurality of band tomographic images for each frequency band to generate band composite two-dimensional images, performs weighting and frequency composition on the band composite two-dimensional images for each frequency band to generate a composite two-dimensional image.

The generation of the above-mentioned composite two-dimensional image makes it possible to easily find a structure such as an abnormal shadow. It is desirable to make the structure easier to find.

SUMMARY OF THE INVENTION

The present disclosure has been made in view of the above-mentioned problems and an object of the present disclosure is to make it easier to find a structure included in an object using a composite two-dimensional image.

According to the present disclosure, there is provided an image processing device comprising: a combination unit that generates a plurality of composite two-dimensional images from a plurality of tomographic images acquired by performing tomosynthesis imaging on an object, using different generation methods. The combination unit generates a first composite two-dimensional image having a quality corresponding to a two-dimensional image acquired by simple imaging or a second composite two-dimensional image in which a structure included in the object has been highlighted as at least one of the plurality of composite two-dimensional images.

The "composite two-dimensional image" is a pseudo two-dimensional image generated by combining a plurality of tomographic images. The composite two-dimensional image is obtained by combining a plurality of tomographic images with different distances (positions in a height direction) from a detection surface of a radiation detector to a radiation source using, for example, an addition method, an averaging method, a maximum intensity projection method, or a minimum intensity projection method. In addition, the composite two-dimensional image can be generated by the methods described in U.S. Pat. No. 8,983,156B to U.S. Pat. No. 9,792,703B.

In the image processing device according to the present disclosure, the combination unit may generate the plurality of composite two-dimensional images including the first composite two-dimensional image and the second composite two-dimensional image.

In the image processing device according to the present disclosure, the combination unit may perform frequency decomposition on the plurality of tomographic images to generate a plurality of band tomographic images indicating frequency components in each of a plurality of frequency bands for each of a plurality of tomographic planes of the object, combine the plurality of band tomographic images for each frequency band to generate band composite two-dimensional images, and perform weighting and frequency composition on the band composite two-dimensional images for each frequency band to generate the first composite two-dimensional image.

In the image processing device according to the present disclosure, the combination unit may generate the second composite two-dimensional image on the basis of tomographic images in which structures have been detected among the plurality of tomographic images.

The image processing device according to the present disclosure may further comprise an image quality adjustment unit that performs an image quality adjustment process for matching a quality of a past radiographic image of an object which is the same as the object and a quality of at least one of the plurality of composite two-dimensional images.

In addition to the two-dimensional image acquired by the simple imaging, the first composite two-dimensional image acquired in the past may be used as the past radiographic image.

In the image processing device according to the present disclosure, the image quality adjustment unit may further perform an image quality adjustment process for matching the quality of the plurality of composite two-dimensional images.

The image processing device according to the present disclosure may further comprise an identification information giving unit that gives identification information for identifying the plurality of composite two-dimensional images to each of the composite two-dimensional images.

According to the present disclosure, there is provided an image display device that displays the plurality of composite two-dimensional images generated by the image processing device according to the present disclosure. The image display device comprises a display control unit that displays at least one of the plurality of composite two-dimensional images.

In the image display device according to the present disclosure, the display control unit may display the plurality of composite two-dimensional images side by side, display the plurality of composite two-dimensional images so as to be switched, or display the plurality of composite two-dimensional images so as to be superimposed.

In the image display device according to the present disclosure, the display control unit may display a different part between the plurality of composite two-dimensional images so as to be highlighted.

In the image display device according to the present disclosure, the display control unit may display the first composite two-dimensional image and a past radiographic image of an object which is the same as the object side by side or may display the first composite two-dimensional image and the past radiographic image so as to be switched.

In the image display device according to the present disclosure, the display control unit may display the second composite two-dimensional image and the plurality of tomographic images side by side or may display the second composite two-dimensional image and the plurality of tomographic images so as to be superimposed.

According to the present disclosure, there is provided an image processing method comprising: in a case in which a plurality of composite two-dimensional images are generated from a plurality of tomographic images acquired by performing tomosynthesis imaging on an object by different generation methods, generating a first composite two-dimensional image having a quality corresponding to a two-dimensional image acquired by simple imaging or a second composite two-dimensional image in which a structure included in the object has been highlighted as at least one of the plurality of composite two-dimensional images.

According to the present disclosure, there is provided an image display method for displaying the plurality of composite two-dimensional images generated by the image processing method according to the present disclosure. The image display method comprises displaying at least one of the plurality of composite two-dimensional images.

In addition, programs that cause a computer to perform the image processing method and the image display method according to the present disclosure may be provided.

Another image processing device according to the present disclosure comprises a memory that stores commands to be executed by a computer and a processor configured to execute the stored commands. The processor performs a process of, in a case in which a plurality of composite two-dimensional images are generated from a plurality of tomographic images acquired by performing tomosynthesis imaging on an object by different generation methods, generating a first composite two-dimensional image having a quality corresponding to a two-dimensional image acquired by simple imaging or a second composite two-dimensional image in which a structure included in the object has been highlighted as at least one of the plurality of composite two-dimensional images.

Another image display device according to the present disclosure comprises a memory that stores commands to be executed by a computer and a processor configured to execute the stored commands. The processor performs a process of displaying at least one of the plurality of composite two-dimensional images generated by the image processing method according to the present disclosure.

According to the present disclosure, since a plurality of generated composite two-dimensional images are displayed, it is possible to more easily find a structure using the composite two-dimensional images.

DETAILED DESCRIPTION

Figure 1:
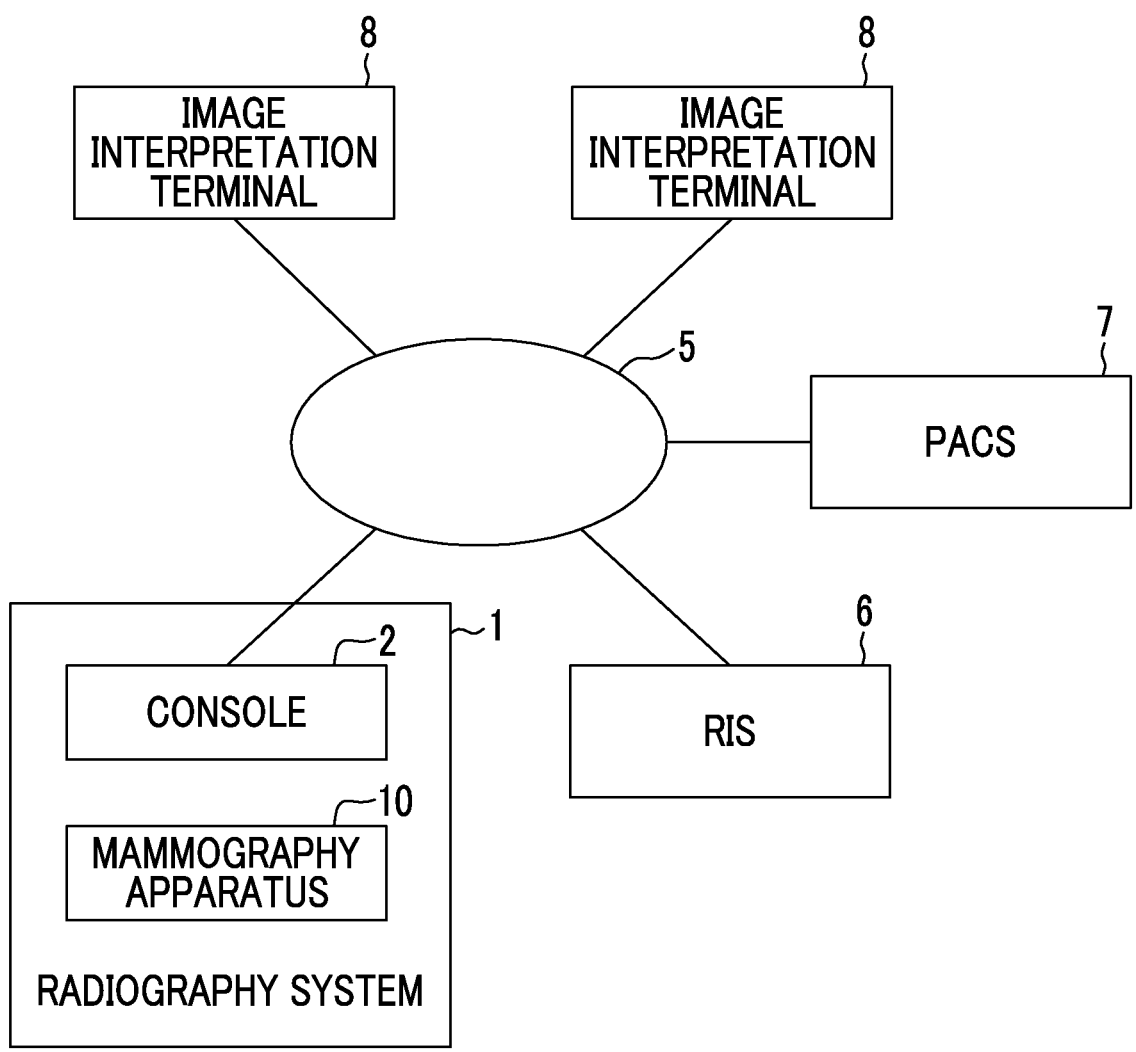
FIG. 1 is a diagram schematically illustrating a configuration of a radiographic image interpretation system to which an image processing device and an image display device according to an embodiment of the present disclosure are applied.

Hereinafter, embodiments of the present disclosure will be described with reference to the drawings. FIG. 1 is a diagram schematically illustrating a configuration of a radiographic image interpretation system to which an image processing device and an image display device according to an embodiment of the present disclosure are applied. As illustrated in FIG. 1, in the radiographic image interpretation system according to this embodiment, a radiography system 1 including a console 2 and a mammography apparatus 10, a radiology information system (RIS) 6, a picture archiving and communication system (PACS) 7, and a plurality of image interpretation terminals (two image interpretation terminals in FIG. 1) 8 are connected through a network 5 so as to communicate with each other.

Figure 2:
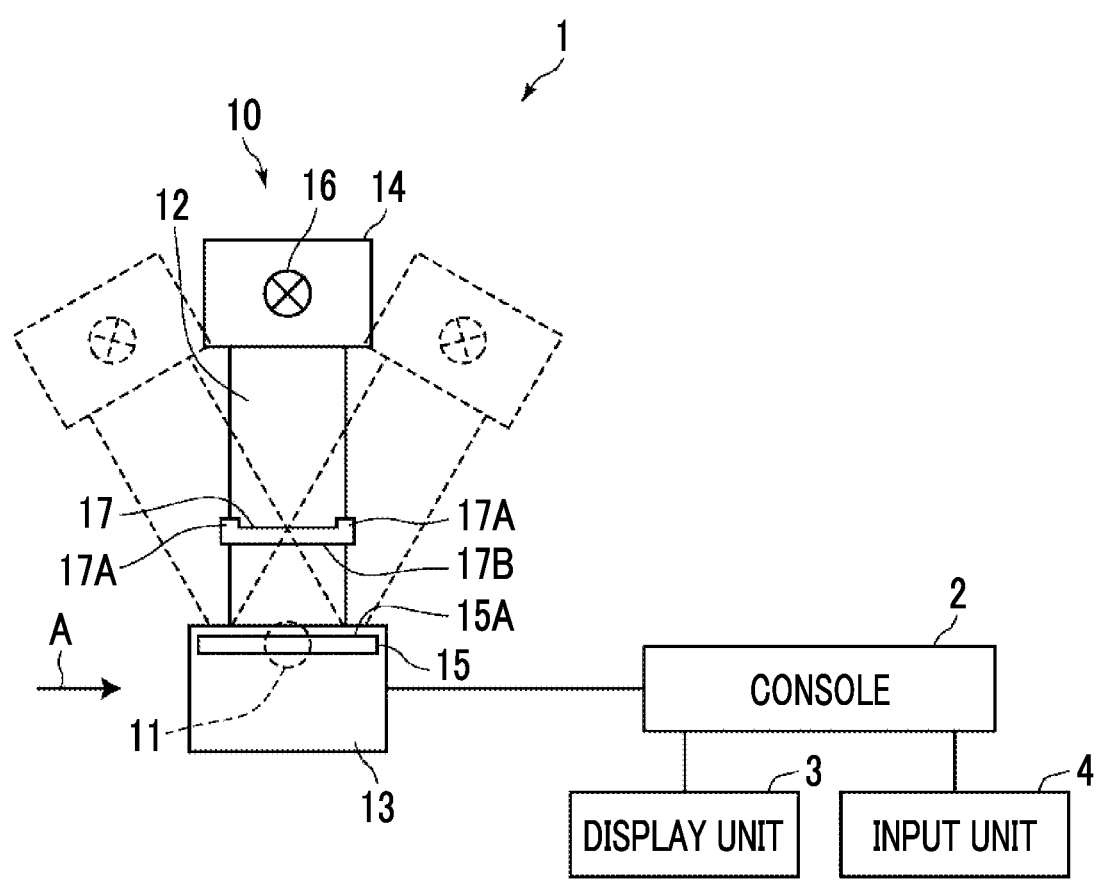
FIG. 2 is a diagram schematically illustrating a configuration of a radiography system.
Figure 3:
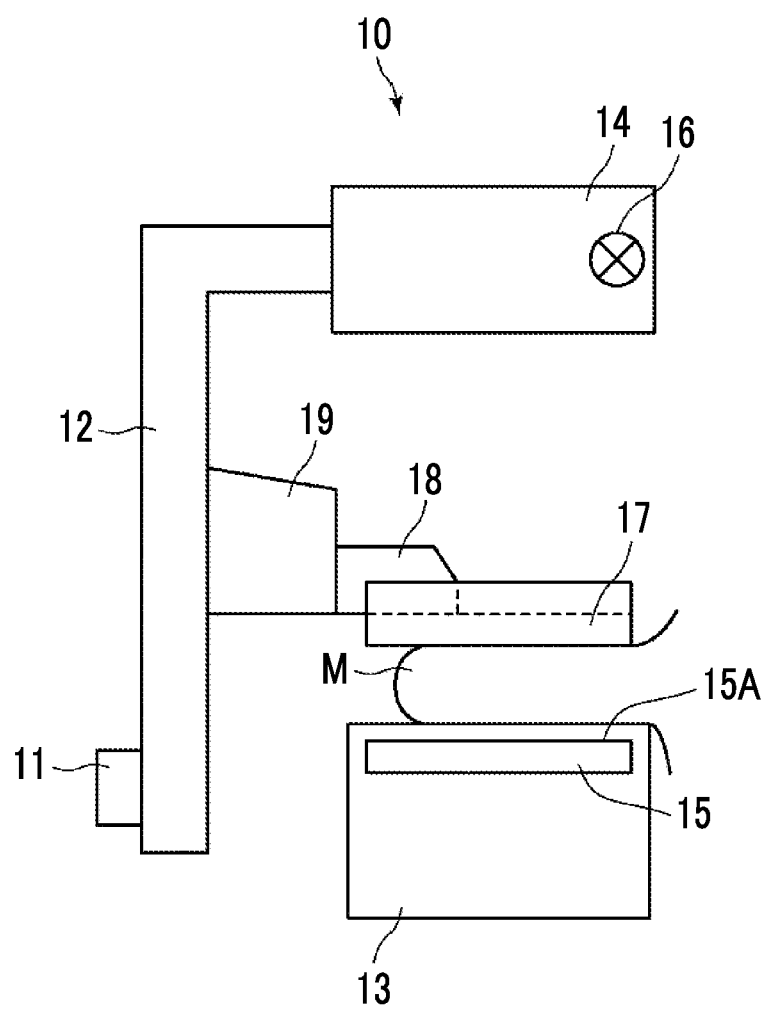
FIG. 3 is a diagram illustrating a mammography apparatus as viewed from a direction of an arrow A in FIG. 2.

FIG. 2 is a diagram schematically illustrating a configuration of the radiography system and FIG. 3 is a diagram illustrating the mammography apparatus included in the radiography system as viewed from the direction of an arrow A in FIG. 2.

As illustrated in FIG. 2, the radiography system 1 includes the console 2 and the mammography apparatus 10. The console 2 comprises a display unit 3 and an input unit 4. The console 2 is connected to the RIS 6 and the PACS 7 through the network 5 so as to communicate therewith.

The radiography system 1 according to this embodiment has a function of capturing the images of a breast M using the mammography apparatus 10 on the basis of a command (imaging order) input from the RIS 6 through the console 2 in response to an operation of an operator, such as a doctor or a radiology technician, and acquiring a tomographic image and a composite two-dimensional image of the breast M. In this embodiment, the mammography apparatus 10 can perform both tomosynthesis imaging and simple imaging in various imaging directions to generate a tomographic image and a two-dimensional breast image of the breast M. The two-dimensional breast image means a breast image acquired by the simple imaging. An image set including the tomographic image and the composite two-dimensional image generated in the radiography system 1 as described below is transmitted to the PACS 7 and is then stored therein.

The mammography apparatus 10 comprises an arm portion 12 that is connected to a base (not illustrated) by a rotation shaft 11. An imaging table 13 is attached to one end of the arm portion 12 and a radiation emitting unit 14 is attached to the other end of the arm portion 12 so as to face the imaging table 13. The arm portion 12 is configured such that only the end to which the radiation emitting unit 14 is attached can be rotated. Therefore, the imaging table 13 is fixed and only the radiation emitting unit 14 can be rotated. The rotation of the arm portion 12 is controlled by the console 2.

A radiation detector 15, such as a flat panel detector, is provided in the imaging table 13. The radiation detector 15 has a radiation detection surface 15A. In addition, for example, a circuit substrate including a charge amplifier that converts a charge signal read from the radiation detector 15 into a voltage signal, a correlated double sampling circuit that samples the voltage signal output from the charge amplifier, and an analog-digital (AD) conversion unit that converts the voltage signal into a digital signal is provided in the imaging table 13.

The radiation detector 15 can repeatedly perform the recording and reading of a radiographic image and may be a so-called direct-type radiation detector that directly converts radiation into charge or a so-called indirect-type radiation detector that converts radiation into visible light once and converts the visible light into a charge signal. As a method for reading a radiographic image signal, it is desirable to use the following method: a so-called thin film transistor (TFT) reading method which turns on and off a TFT switch to read a radiographic image signal; or a so-called optical reading method which emits reading light to read a radiographic image signal. However, the reading method is not limited thereto and other methods may be used.

A radiation source 16 is accommodated in the radiation emitting unit 14. The radiation source 16 emits, for example, X-rays as radiation. The console 2 controls the timing when the radiation source 16 emits the radiation and the radiation generation conditions of the radiation source 16, that is, the selection of target and filter materials, a tube voltage, an irradiation time, and the like.

Further, the arm portion 12 is provided with a compression plate 17 that presses and compresses the breast M, a support portion 18 that supports the compression plate 17, and a movement mechanism 19 that moves the support portion 18 in the vertical direction in FIGS. 2 and 3. An interval between the compression plate 17 and the imaging table 13, that is, a compression thickness is input to the console 2. In addition, the compression plates 17 having a plurality of sizes and shapes corresponding to the types of imaging are prepared. Therefore, the compression plate 17 is attached to the support portion 18 so as to be interchangeable. Further, side walls 17A are formed on the left and right edges of the compression plate 17 in FIG. 2. The side walls 17A are formed in order to reduce the pain of a patient in a case in which the breast M compressed by a compression surface 17B of the compression plate 17 protrudes from the compression plate 17.

The display unit 3 is a display device, such as a cathode ray tube (CRT) or a liquid crystal display, and displays messages required for operations in addition to a tomographic image and a composite two-dimensional image which will be described below. The display unit 3 may include a speaker that outputs sound.

The input unit 4 consists of a keyboard, a mouse, or a touch-panel-type input device and receives commands to operate the mammography apparatus 10 from the operator. In addition, the input unit 4 receives the input of various kinds of information required for tomosynthesis imaging, such as imaging conditions, and a command to correct information. In this embodiment, each unit of the mammography apparatus 10 is operated according to the information input by the operator through the input unit 4.

An imaging program for performing, for example, tomosynthesis imaging and an image processing program according to this embodiment are installed in the console 2. The console 2 corresponds to the image processing device according to this embodiment. In this embodiment, the console 2 may be a workstation or a personal computer that is directly operated by the operator or a server computer that is connected to them through a network. The imaging program is stored in a storage device of a server computer connected to the network or a network storage in a state in which it can be accessed from the outside and is downloaded and installed in the computer as required. Alternatively, the imaging control program is recorded on a recording medium, such as a digital versatile disc (DVD) or a compact disc read only memory (CD-ROM), is distributed, and is installed in a computer from the recording medium.

Figure 4:
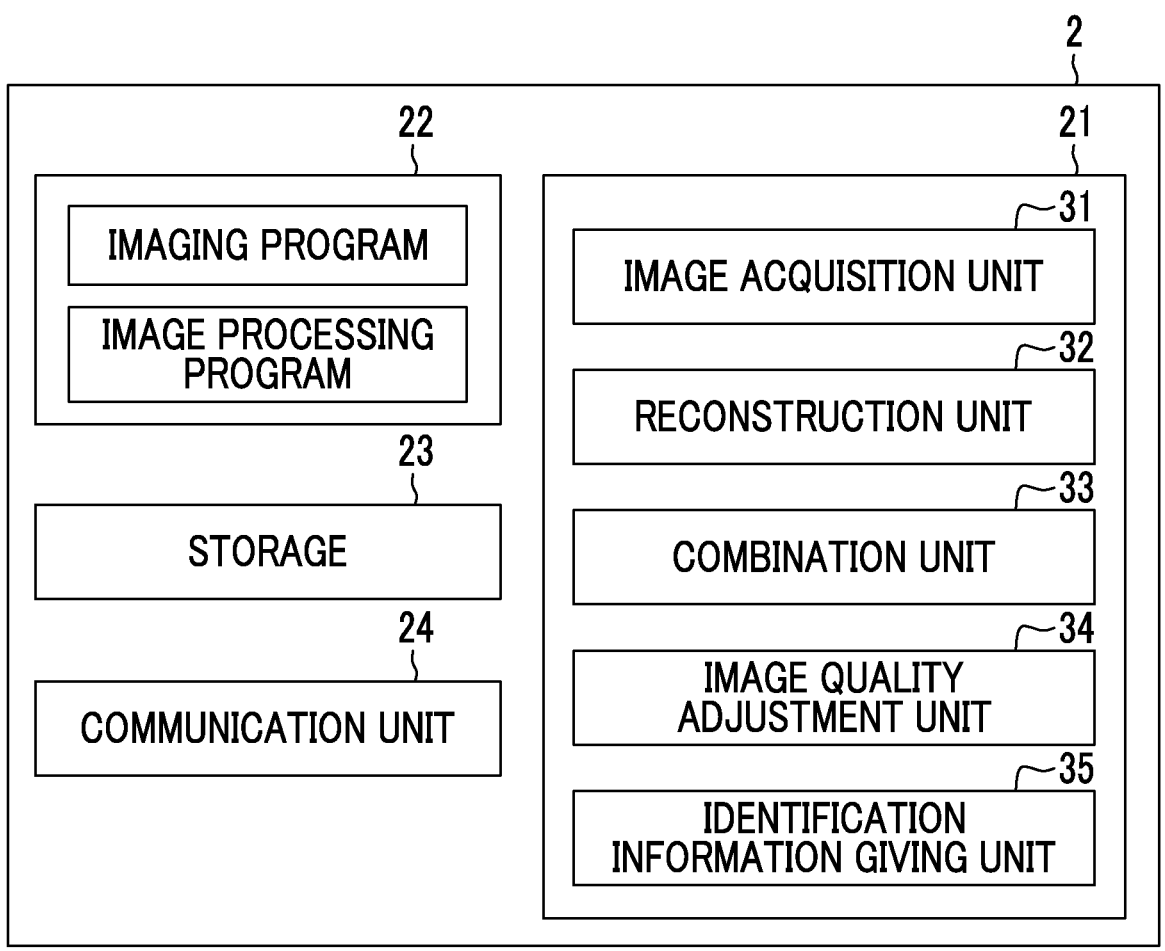
FIG. 4 is a diagram schematically illustrating a configuration of the image processing device implemented by installing an imaging program and an image processing program in a computer forming a console.

FIG. 4 is a diagram schematically illustrating the configuration of the image processing device that is implemented by installing the imaging program and the image processing program in a computer forming the console 2. As illustrated in FIG. 4, the image processing device comprises a central processing unit (CPU) 21, a memory 22, a storage 23, and a communication unit 24 as a standard computer configuration.

The storage 23 consists of a storage device, such as a hard disk drive or a solid state drive (SSD), and stores various kinds of information including the imaging program and the image processing program for driving each unit of the mammography apparatus 10 to perform the tomosynthesis imaging. Further, for example, projection images acquired by imaging, and tomographic images and a plurality of composite two-dimensional images generated as described below are stored in the storage 23.

The communication unit 24 is a network interface that controls the transmission of various kinds of information through the network 5.

The memory 22 temporarily stores, for example, the imaging program and the image processing program stored in the storage 23 in order to cause the CPU 21 to perform various processes. The imaging program defines, as a process to be executed by the CPU 21, an image acquisition process that causes the mammography apparatus 10 to perform tomosynthesis imaging to acquire a plurality of projection images of the breast M corresponding to each of a plurality of radiation source positions. The image processing program defines the following processes as the processes to be executed by the CPU 21: a reconstruction process that reconstructs the plurality of projection images to generate a plurality of tomographic images in each of a plurality of tomographic planes of the breast M which is an object; a combination process that generates a plurality of composite two-dimensional images from the plurality of tomographic images using different generation methods; an image quality adjustment process that matches the quality of the past radiographic image and at least one of the plurality of composite two-dimensional images of the same object; and an identification information giving process that gives identification information for identifying the plurality of composite two-dimensional images to each of the composite two-dimensional images.

The CPU 21 of the console 2 performs a process according to the imaging program such that the CPU 21 functions as an image acquisition unit 31. In addition, the CPU 21 performs a process according to the image processing program to function as a reconstruction unit 32, a combination unit 33, an image quality adjustment unit 34, and an identification information giving unit 35.

Figure 5:
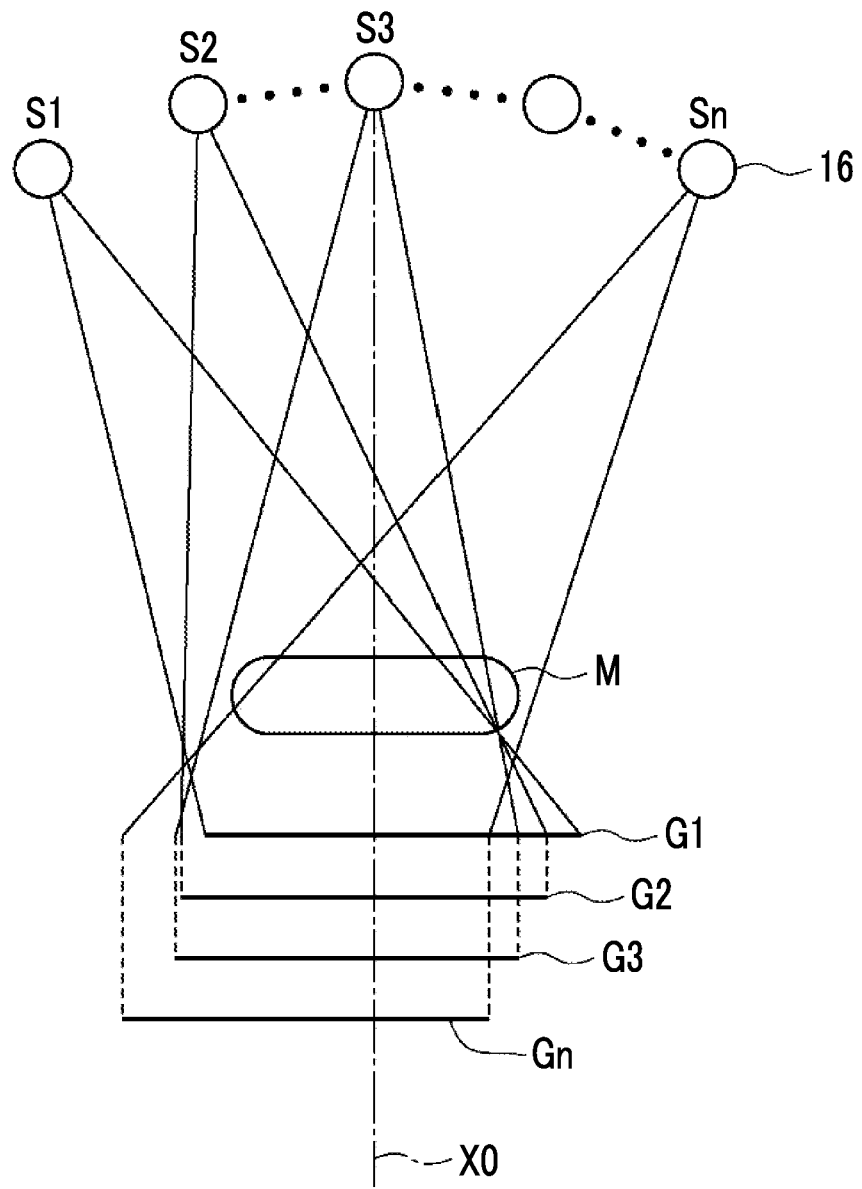
FIG. 5 is a diagram illustrating the acquisition of projection images.

The image acquisition unit 31 rotates the arm portion 12 around the rotation shaft 11 to move the radiation source 16, irradiates the breast M with radiation at a plurality of radiation source positions caused by the movement of the radiation source 16 according to imaging conditions for tomosynthesis imaging, detects the radiation transmitted through the breast M using the radiation detector 15, and acquires a plurality of projection images Gi (i=1 to n, where n is the number of radiation source positions and is, for example, 15) at the plurality of radiation source positions. FIG. 5 is a diagram illustrating the acquisition of the projection images Gi. As illustrated in FIG. 5, the radiation source 16 is moved to each of radiation source positions S1, S2, . . . , Sc, . . . , and Sn. The radiation source 16 is driven at each radiation source position to irradiate the breast M with radiation. The radiation detector 15 detects the radiation transmitted through the breast M to acquire projection images G1, G2, . . . , Gc, . . . , and Gn corresponding to the radiation source positions S1 to Sn, respectively. Here, the radiation source position Sc illustrated in FIG. 5 is a radiation source position where an optical axis X0 of the radiation emitted from the radiation source 16 is orthogonal to the detection surface 15A of the radiation detector 15. Hereinafter, in some cases, the radiation source position Sc is referred to as a reference radiation source position Sc. At each of the radiation source positions S1 to Sn, the same dose of radiation is emitted to the breast M. The plurality of acquired projection images Gi are stored in the storage 23.

Figure 6:
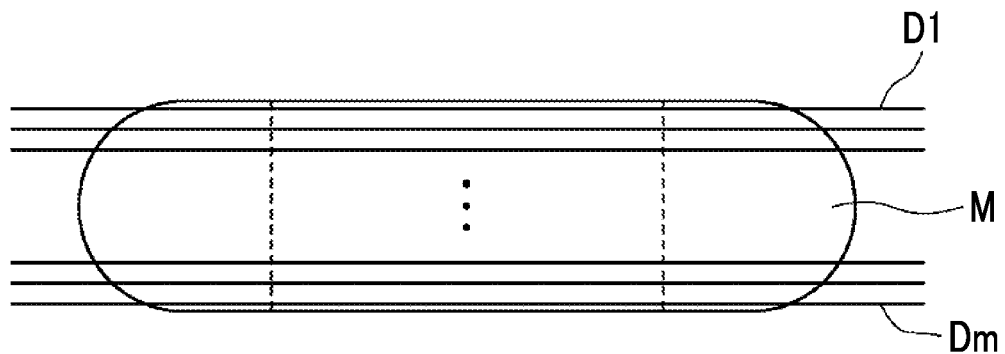
FIG. 6 is a diagram illustrating the generation of tomographic images.

The reconstruction unit 32 reconstructs the projection images Gi to generate the tomographic images in which the desired tomographic planes of the breast M have been highlighted. Specifically, the reconstruction unit 32 reconstructs the plurality of projection images Gi using a known back projection method, such as a simple back projection method or a filtered back projection method, to generate a plurality of tomographic images Dj (j=1 to m) in each of the plurality of tomographic planes of the breast M as illustrated in FIG. 6. In this case, a three-dimensional coordinate position in a three-dimensional space including the breast M is set, pixel values at corresponding pixel positions in the plurality of projection images Gi are reconstructed for the set three-dimensional coordinate position, and pixel values at the coordinate positions are calculated. A three-dimensional image of the breast M is configured by the plurality of tomographic images Dj generated by the reconstruction.

The combination unit 33 generates a plurality of composite two-dimensional images CGk (k=an integer equal to or greater than 2) on the basis of the plurality of tomographic images Dj using different generation methods. In addition, in this embodiment, it is assumed that two first and second composite two-dimensional images CG1 and CG2 are generated. Here, a composite two-dimensional image CGk is a pseudo two-dimensional image corresponding to a simple two-dimensional image that is captured by irradiating the breast M with radiation emitted at the reference radiation source position Sc. In this embodiment, the combination unit 33 generates the first composite two-dimensional image CG1 having image quality corresponding to the two-dimensional image acquired by simple imaging using the method described in JP2018-029746A. In addition, the combination unit 33 generates the second composite two-dimensional image CG2 in which structures, such as abnormal shadows, included in the breast M have been highlighted, using the method described in U.S. Pat. No. 8,983,156B or U.S. Pat. No. 9,792,703B.

Here, the combination unit 33 generates the first composite two-dimensional image CG1 as follows according to the method described in JP2018-029746A. First, the combination unit 33 performs frequency decomposition for each of the plurality of tomographic images Dj to derive a plurality of band tomographic images indicating frequency components in each of a plurality of frequency bands for each of the plurality of tomographic images Dj. Further, the combination unit 33 combines a plurality of band tomographic images for each frequency band to generate band composite two-dimensional images. For example, an addition method, an averaging method, a maximum intensity projection method, or a minimum intensity projection method can be used as a combination method. The addition method will be described in detail in the generation of the second composite two-dimensional image CG2. Then, the combination unit 33 performs weighting and frequency composition on the band composite two-dimensional images for each frequency band to generate the first composite two-dimensional image CG1.

Figure 7:
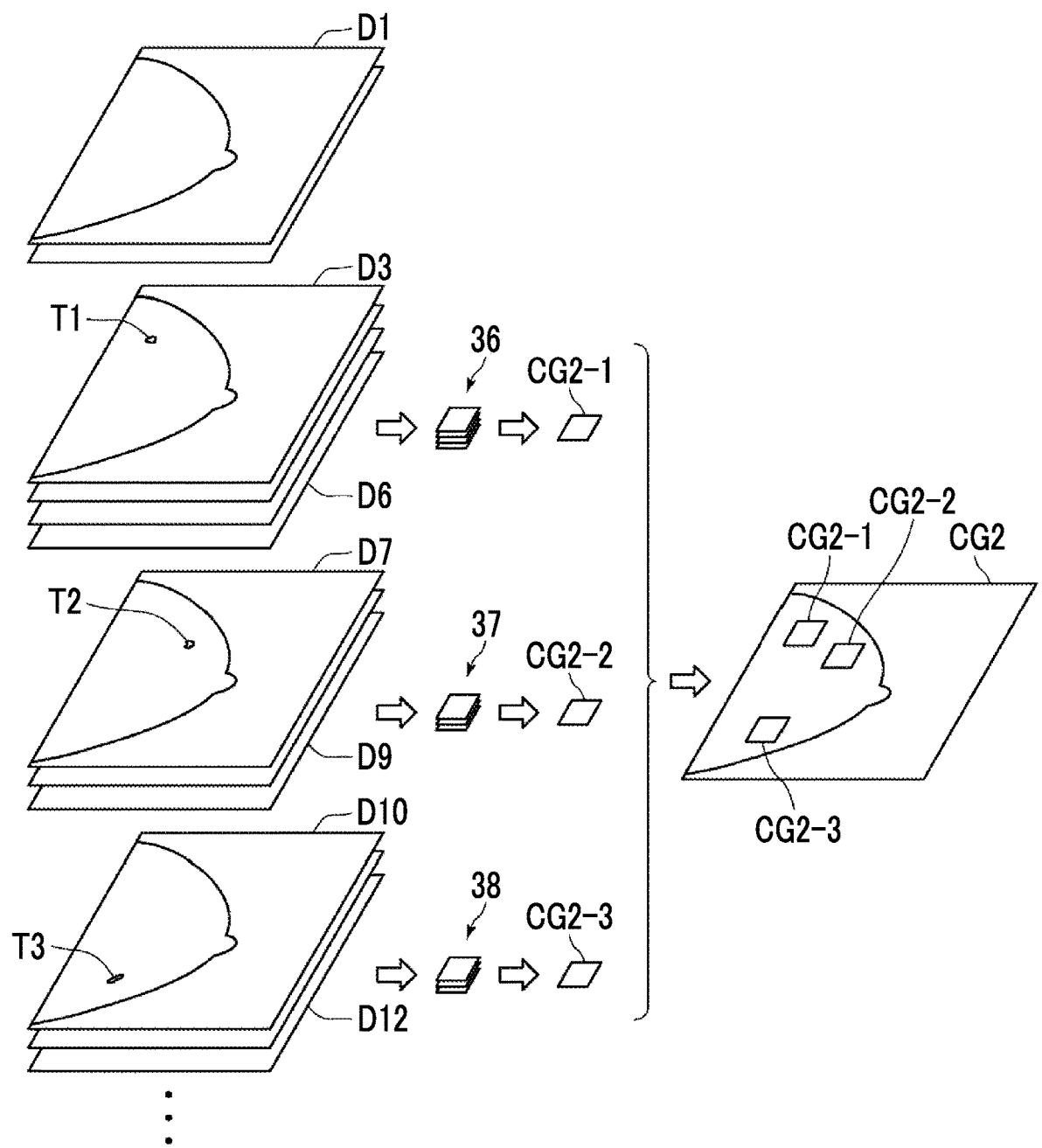
FIG. 7 is a diagram illustrating the generation of a second composite two-dimensional image.

In addition, the combination unit 33 generates the second composite two-dimensional image CG2 as follows according to the method described in U.S. Pat. No. 8,983,156B. FIG. 7 is a diagram illustrating the generation of the second composite two-dimensional image CG2. First, the combination unit 33 detects a region of interest including structures, such as abnormal shadows, from each of the plurality of tomographic images Dj using CAD. In addition, a detection unit that detects structures using CAD may be provided separately from the combination unit 33 and may detect the structures from the plurality of tomographic images Dj. In this embodiment, it is assumed that three abnormal shadows T1 to T3 are detected as structures from the plurality of tomographic images Dj. Since a lesion is present in the thickness direction of the breast M, the abnormal shadows T1 to T3 are present across a plurality of tomographic images. For example, the abnormal shadow T1 is present across four tomographic images D3 to D6, the abnormal shadow T2 is present across three tomographic images D7 to D9, and the abnormal shadow T3 is present across three tomographic images D10 to D12.

The combination unit 33 sets a region of interest including the abnormal shadows T1 to T3 in the plurality of tomographic images. As a result, as illustrated in FIG. 7, a region-of-interest group 36 consisting of four regions of interest for each of the tomographic images D3 to D6 is acquired for the abnormal shadow T1. In addition, a region-of-interest group 37 consisting of three regions of interest for each of the tomographic images D7 to D9 is acquired for the abnormal shadow T2. A region-of-interest group 38 consisting of three regions of interest for each of the tomographic images D10 to D12 is acquired for the abnormal shadow T3.

Then, the combination unit 33 combines only the regions of interest using, for example, the addition method to generate a composite two-dimensional image of the regions of interest. The addition method is a method that weights and adds the values of the corresponding pixels in each of the region-of-interest groups 36 to 38 along a viewing direction from the reference radiation source position Sc to the radiation detector 15, that is, the optical axis XO illustrated in FIG. 5 in a state in which the plurality of tomographic images Dj are stacked. In the addition method, a weight for each pixel during the weighting and addition is set to 1/x in a case in which x is the number of regions of interest included in the region-of-interest groups 36 to 38. Further, a method for generating the composite two-dimensional image of the regions of interest is not limited to the addition method and a known technique, such as an averaging method, a minimum intensity projection method, or a maximum intensity projection method, can be applied. As a result, the combination unit 33 generates region-of-interest composite two-dimensional images CG2-1, CG2-2, and CG2-3 for the region-of-interest groups 36 to 38, respectively.

Further, the combination unit 33 combines the region-of-interest composite two-dimensional images CG2-1, CG2-2, and CG2-3 with a predetermined two-dimensional image to generate the second composite two-dimensional image CG2. A projection image acquired in a case in which the radiation source 16 is at the reference radiation source position Sc may be used as the predetermined two-dimensional image. In addition, a simple two-dimensional image separately acquired by simple imaging may be used.

Further, the combination unit 33 may generate the second composite two-dimensional image CG2, in which structures have been highlighted, by performing combination on the basis of the tomographic images in which the structures have been detected using the method described in U.S. Pat. No. 9,792,703B instead of the method described in U.S. Pat. No. 8,983,156B.

The image quality adjustment unit 34 performs an image quality adjustment process for matching the quality of the past radiographic image of the patient whose first and second composite two-dimensional images CG1 and CG2 have been generated with the quality of at least one of the first composite two-dimensional image CG1 or the second composite two-dimensional image CG2. In this embodiment, it is assumed that an image quality adjustment process for matching the quality of the past radiographic image and the quality of the first composite two-dimensional image CG1 is performed. Specifically, for example, as the image quality adjustment process, a density conversion process and a contrast adjustment process are performed on the first composite two-dimensional image CG1 such that the past radiographic image and the first composite two-dimensional image CG1 have the same density and contrast. In addition, the image quality adjustment process may be performed on the past radiographic image. For example, the method described in JP2009-136376A is used as the image quality adjustment process. The process described in JP2009-136376A derives, for example, conditions for matching image characteristics, such as the density and contrast of regions including structures, in two images and matches the image characteristics of the two images on the basis of the derived conditions. In addition, parameters of image processing performed on the past radiographic image may be acquired and the image quality adjustment process may be performed on the first composite two-dimensional image CG1 according to the acquired parameters.

Further, a two-dimensional image acquired by simple imaging or a first composite two-dimensional image acquired in the past examination may be used as the past radiographic image.

Figure 8:
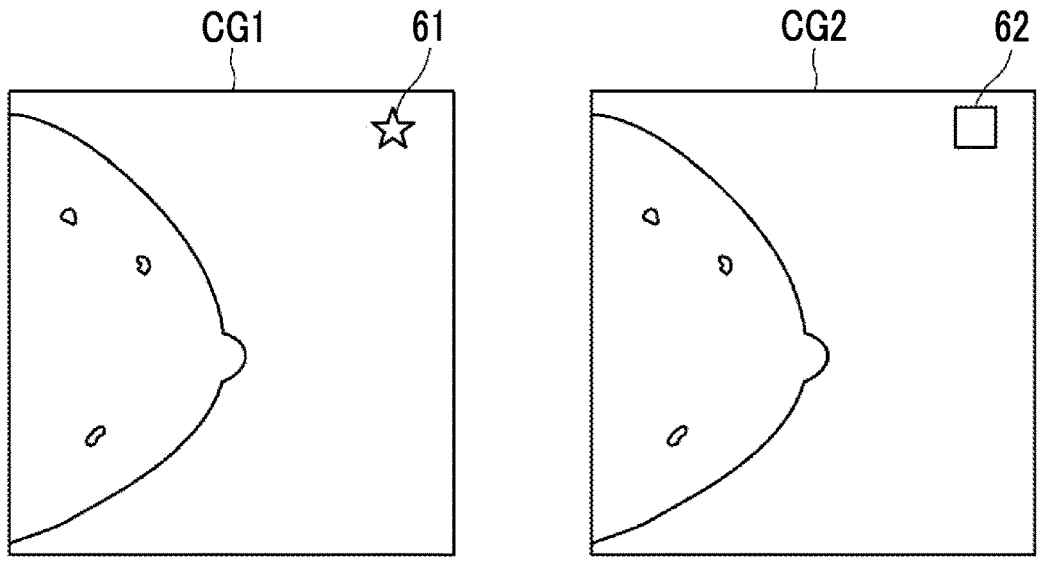
FIG. 8 is a diagram illustrating first and second composite two-dimensional images to which markers are added as identification information.

The identification information giving unit 35 gives identification information for identifying a plurality of composite two-dimensional images to each of the composite two-dimensional images. Specifically, the identification information giving unit 35 gives first identification information indicating that the first composite two-dimensional image CG1 has a quality corresponding to the two-dimensional image acquired by simple imaging to the first composite two-dimensional image CG1. Further, the identification information giving unit 35 provides second identification information indicating that a structure is easy to see to the second composite two-dimensional image CG2. For example, different types of markers can be used as the first identification information and the second identification information. FIG. 8 is a diagram illustrating the first and second composite two-dimensional images CG1 and CG2 to which a marker is added as the identification information. As illustrated in FIG. 8, an asterisk marker 61 is added to the first composite two-dimensional image CG1 and a square marker 62 is added to the second composite two-dimensional image CG2. The shape of the marker is not limited to those illustrated in FIG. 8. Further, instead of the markers, the first identification information and the second identification information may be texts indicating methods for generating the first composite two-dimensional image CG1 and the second composite two-dimensional image CG2, respectively.

An image set including the plurality of tomographic images Dj and the first and second composite two-dimensional images CG1 and CG2 generated as described above is transmitted to the PACS 7 through the network 5 by the communication unit 24 in response to a command from the input unit 4. In this case, the image set includes image identification information (for example, an image ID, a patient name, and an imaging date and time) for uniquely identifying the image set. The image set transmitted to the PACS 7 is stored in the PACS 7. The image set may include at least one of the plurality of projection images Gi.

The image interpretation terminal 8 is a computer that is used by a radiologist who interprets a radiographic image to interpret a radiographic image and to make an interpretation report. The image interpretation terminal 8 includes an image display device according to an embodiment of the present disclosure. Therefore, an image display program according to this embodiment is installed in the image interpretation terminal 8. The image display program is stored in a storage device of a server computer connected to the network or a network storage in a state in which it can be accessed from the outside and is downloaded and installed in the computer as required. Alternatively, the program is recorded on a recording medium, such as a DVD or a CD-ROM, is distributed, and is installed in the computer from the recording medium.

Figure 9:
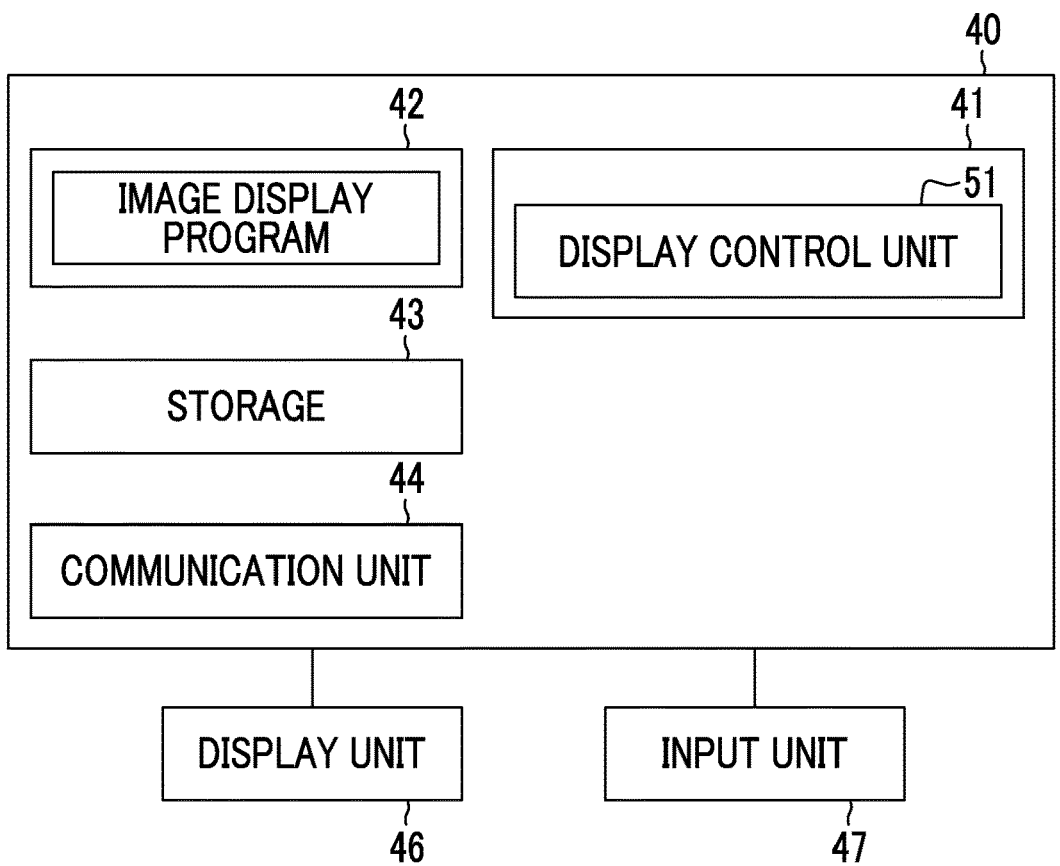
FIG. 9 is a diagram schematically illustrating a configuration of the image display device implemented by installing an image display program in the computer.

FIG. 9 is a diagram schematically illustrating a configuration of the image display device implemented by installing the image display program in the computer. As illustrated in FIG. 9, an image display device 40 comprises a CPU 41, a memory 42, a storage 43, and a communication unit 44 as a standard computer configuration. Further, the image display device 40 is connected to a display unit 46, such as a high-definition liquid crystal display for interpreting a radiographic image, and an input unit 47, such as a keyboard or a mouse.

The storage 43 consists of a storage device, such as a hard disk drive or an SSD, and stores various kinds of information including the image display program according to this embodiment.

The memory 42 temporarily stores, for example, the image display program stored in the storage 43 in order to cause the CPU 41 to perform various processes. The image display program defines, as a process to be executed by the CPU 41, a display control process that displays the first composite two-dimensional image CG1 and the second composite two-dimensional image CG2 included in the image set acquired from the PACS 7 on the display unit 46.

Then, the CPU 41 performs the process according to the image display program such that the CPU 41 functions as a display control unit 51.

The communication unit 44 is a network interface that controls the transmission of various kinds of information through the network 5. In a case in which the image identification information of the acquired image set is input from the input unit 47, the communication unit 44 transmits the input image identification information to the PACS 7 through the network 5. The PACS 7 transmits the image set corresponding to the received image identification information to the image interpretation terminal 8 through the network 5. Then, the communication unit 44 receives the image set and stores the image set in the storage 43.

Figure 10:
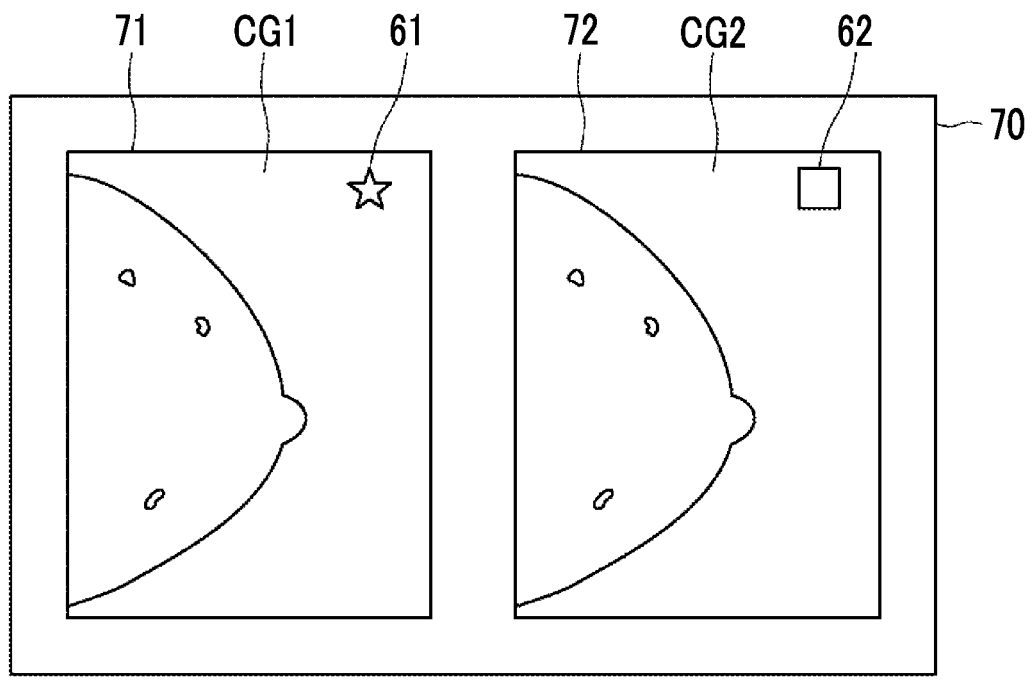
FIG. 10 is a diagram illustrating a display screen for the first and second composite two-dimensional images.

The display control unit 51 displays at least one of the first composite two-dimensional image CG1 or the second composite two-dimensional image CG2 included in the acquired image set on the display unit 46. In this embodiment, it is assumed that both the first composite two-dimensional image CG1 and the second composite two-dimensional image CG2 are displayed. FIG. 10 is a diagram illustrating a composite two-dimensional image display screen. As illustrated in FIG. 10, a display screen 70 includes a first display region 71 and a second display region 72 for displaying the first composite two-dimensional image CG1 and the second composite two-dimensional image CG2, respectively. Then, in a case in which a command to start image interpretation is input to the image interpretation terminal 8 by the radiologist who is an operator, the display control unit 51 displays the first composite two-dimensional image CG1 and the second composite two-dimensional image CG2 in the first and second display regions 71 and 72, respectively, as illustrated in FIG. 10. Then, the first composite two-dimensional image CG1 and the second composite two-dimensional image CG2 are displayed side by side on the display unit 46. The asterisk marker 61 is added to the first composite two-dimensional image CG1 and the square marker 62 is added to the second composite two-dimensional image CG2.

The radiologist can interpret the displayed first and second composite two-dimensional images CG1 and CG2 to check structures such as abnormal shadow included in the breast M. Further, the radiologist inputs a command to acquire the past images of the same patient from the PACS 7 to the image interpretation terminal 8 for follow-up observation, if necessary. Then, the past image of the same patient is transmitted to the image interpretation terminal 8 and then displayed on the display unit 46 by the display control unit 51.

Figure 11:
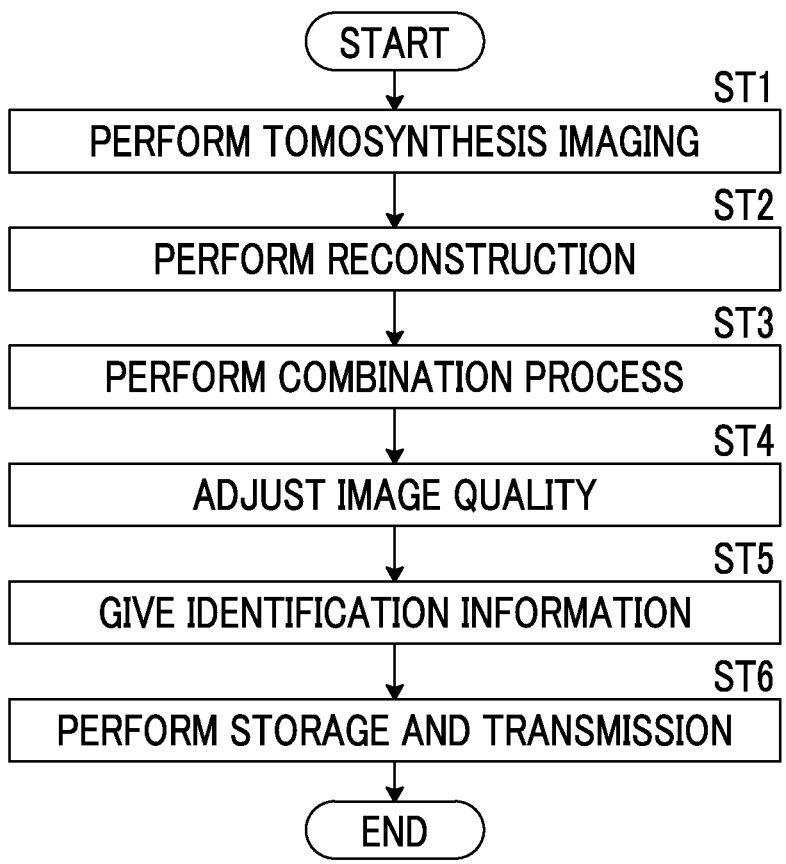
FIG. 11 is a flowchart illustrating a process performed in the image processing device according to this embodiment.

Next, a process performed in this embodiment will be described. FIG. 11 is a flowchart illustrating the process performed by the image processing device according to this embodiment. First, the process is started by the input of an imaging command by the operator and the image acquisition unit 31 commands the mammography apparatus 10 to perform the tomosynthesis imaging. Then, the mammography apparatus 10 performs the tomosynthesis imaging on the breast M (Step ST1). A plurality of projection images Gi are acquired by the tomosynthesis imaging. Then, the reconstruction unit 32 reconstructs the plurality of projection images Gi acquired by the tomosynthesis imaging (Step ST2). Then, a plurality of tomographic images Dj are generated. Then, the combination unit 33 performs the combination process using the plurality of tomographic images Dj (Step ST3). Then, the first and second composite two-dimensional images CG1 and CG2 are generated from the plurality of tomographic images Dj by different generation methods.

Then, the image quality adjustment unit 34 performs the image quality adjustment process for matching the quality of the past radiographic image of the same patient and the quality of at least one of the plurality of composite two-dimensional images (Step ST4). Further, the identification information giving unit 35 gives identification information for identifying the generation method to the first and second composite two-dimensional images CG1 and CG2 (Step ST5). The first and second composite two-dimensional images CG1 and CG2 are stored in the storage 23 and are transmitted to the PACS 7 by the communication unit 24 (Step ST6). Then, the process ends.

Figure 12:
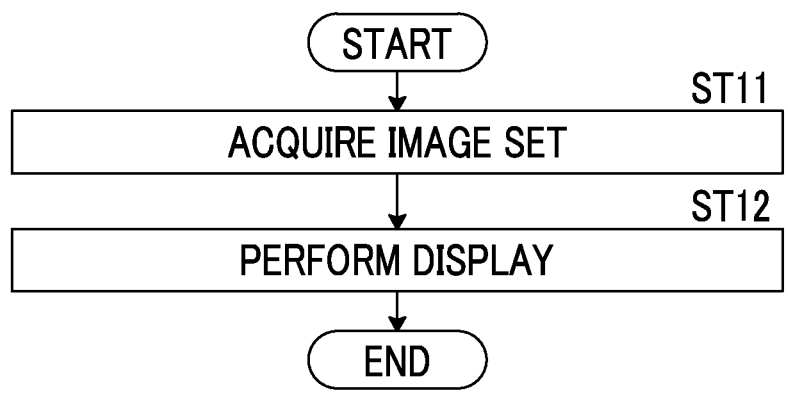
FIG. 12 is a flowchart illustrating a process performed in the image display device according to this embodiment.

FIG. 12 is a flowchart illustrating a process performed by the image display device according to this embodiment. The process is started by the input of an image acquisition command from the image interpretation terminal 8 and the communication unit 44 acquires the image set corresponding to the image identification information transmitted from the PACS 7 (Step ST11). Then, the display control unit 51 displays the first and second composite two-dimensional images CG1 and CG2 included in the image set on the display unit 46 (Step ST12). Then, the process ends.

As described above, in this embodiment, the first and second composite two-dimensional images CG1 and CG2 are generated by different generation methods. Here, the first composite two-dimensional image CG1 has quality corresponding to the two-dimensional image acquired by simple imaging. Further, in the second composite two-dimensional image CG2, the structures are highlighted by, for example, the addition method. Therefore, the display of the first composite two-dimensional image CG1 and the second composite two-dimensional image CG2 makes it possible to compare the appearance of a structure in the two-dimensional image acquired by simple imaging with the appearance of a structure in the composite two-dimensional image generated by, for example, the addition method.

Here, the past image of the same patient may be only the two-dimensional image acquired by simple imaging. In this embodiment, the first composite two-dimensional image CG1 has a quality corresponding to the two-dimensional image acquired by simple imaging. Therefore, according to this embodiment, even in a case in which the past image to be compared for follow-up observation is acquired by simple imaging, the first composite two-dimensional image CG1 makes it possible to perform follow-up observation without a sense of incongruity. Further, in the second composite two-dimensional image CG2, the structure is highlighted such that it is easy to see. Therefore, it is possible to easily observe the structure.

Furthermore, in this embodiment, the identification information for identifying each of the first and second composite two-dimensional images CG1 and CG2 is given to the first and second composite two-dimensional images CG1 and CG2 as the markers 61 and 62. Therefore, the radiologist can easily recognize how each of the two composite two-dimensional images displayed on the display unit 46 is generated. As a result, it is possible to perform image interpretation, considering the best use of the appearance of the composite two-dimensional image.

In the above-described embodiment, the combination unit 33 generates two composite two-dimensional images, that is, the first and second composite two-dimensional images CG1 and CG2. However, the present disclosure is not limited thereto. The combination unit 33 may generate three or more composite two-dimensional images using different generation methods. As a method for generating a composite two-dimensional image other than the method for generating the first and second composite two-dimensional images CG1 and CG2, it is possible to use a composite two-dimensional image which is obtained by adding a plurality of tomographic images and simulates the process of the transmission of radiation through the breast M which is an object. In addition, for example, the following composite two-dimensional images can be used: a composite two-dimensional image obtained by averaging the first composite two-dimensional image CG1 and the second composite two-dimensional image CG2; a composite two-dimensional image derived using only tomographic images for tomographic planes within a specific thickness range of the breast M (for example, tomographic planes within a range of 20 to 30 mm in a thickness of 40 mm); and a composite two-dimensional image obtained by extracting specific structures, such as line structures, from the tomographic images and combining only the extracted structures. Further, only the region-of-interest composite two-dimensional image derived in the process of generating the second composite two-dimensional image CG2 may be used as the composite two-dimensional image. In a case in which three or more composite two-dimensional images are generated, identification information corresponding to the generation method may be given to the generated composite two-dimensional images.

In the above-described embodiment, the first and second composite two-dimensional images CG1 and CG2 are generated. However, the present disclosure is not limited thereto. Either the first composite two-dimensional image CG1 or the second composite two-dimensional image CG2 may be generated. In a case in which three or more composite two-dimensional images are generated, it is not necessary to generate both the first and second composite two-dimensional images CG1 and CG2. Either the first composite two-dimensional image CG1 or the second composite two-dimensional image CG2 may be generated.

Further, in the above-described embodiment, the identification information for identifying each of a plurality of composite two-dimensional images is given. However, the present disclosure is not limited thereto. A composite two-dimensional image may be generated without giving the identification information.

Figure 13:
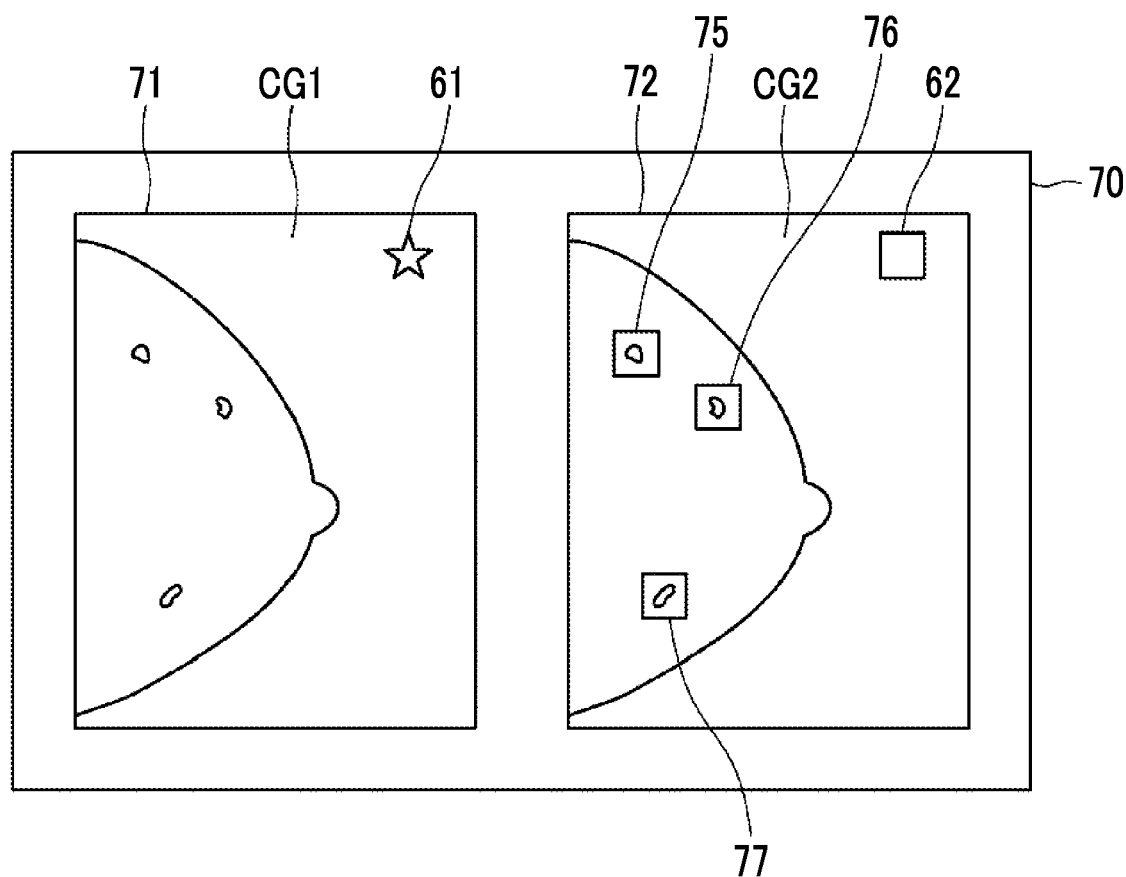
FIG. 13 is a diagram illustrating a display screen on which a different part between the first and second composite two-dimensional images is highlighted.

In the above-described embodiment, the image interpretation terminal 8 displays the first and second composite two-dimensional images CG1 and CG2 side by side. However, in this case, a different part between the first and second composite two-dimensional images CG1 and CG1 may be highlighted. The different part may be a region consisting of pixels in which the difference between corresponding pixels of the first composite two-dimensional image CG1 and the second composite two-dimensional image CG2 is equal to or greater than a predetermined threshold value. FIG. 13 is a diagram illustrating a display screen in which different parts between the first and second composite two-dimensional images CG1 and CG2 are highlighted. As illustrated in FIG. 13, rectangular markers 75 to 77 are added to different parts of the second composite two-dimensional image CG2 from the first composite two-dimensional image CG1 such that the different parts are highlighted. In addition, markers, such as arrows, may be used instead of the rectangular markers 75 to 77. Furthermore, instead of adding the marker, a filtering process for highlighting the different part may be performed. As such, the highlighting of the different part between the first and second composite two-dimensional images CG1 and CG2 makes it possible to easily perform comparative interpretation between the first composite two-dimensional image CG1 and the second composite two-dimensional image CG2.

Further, in the above-described embodiment, the image interpretation terminal 8 displays the first and second composite two-dimensional images CG1 and CG2 side by side. However, the present disclosure is not limited thereto. The first and second composite two-dimensional images CG1 and CG2 may be displayed so as to be switched. Here, structures, such as abnormal shadows, are highlighted in the second composite two-dimensional image CG2. Therefore, in a case in which the first and second composite two-dimensional images CG1 and CG2 are displayed so as to be switched, an image in which structures have been highlighted and an image in which structures have not been highlighted are alternately displayed. Therefore, it is possible to easily check the position of structures on the basis of a difference in the highlight of structures between two images. Further, the first and second composite two-dimensional images CG1 and CG2 may be displayed so as to be superimposed. In a case in which the first and second composite two-dimensional images CG1 and CG2 are displayed so as to be superimposed, the transparency of the first and second composite two-dimensional images CG1 and CG2 may be set to, for example, 50%.

Figure 14:
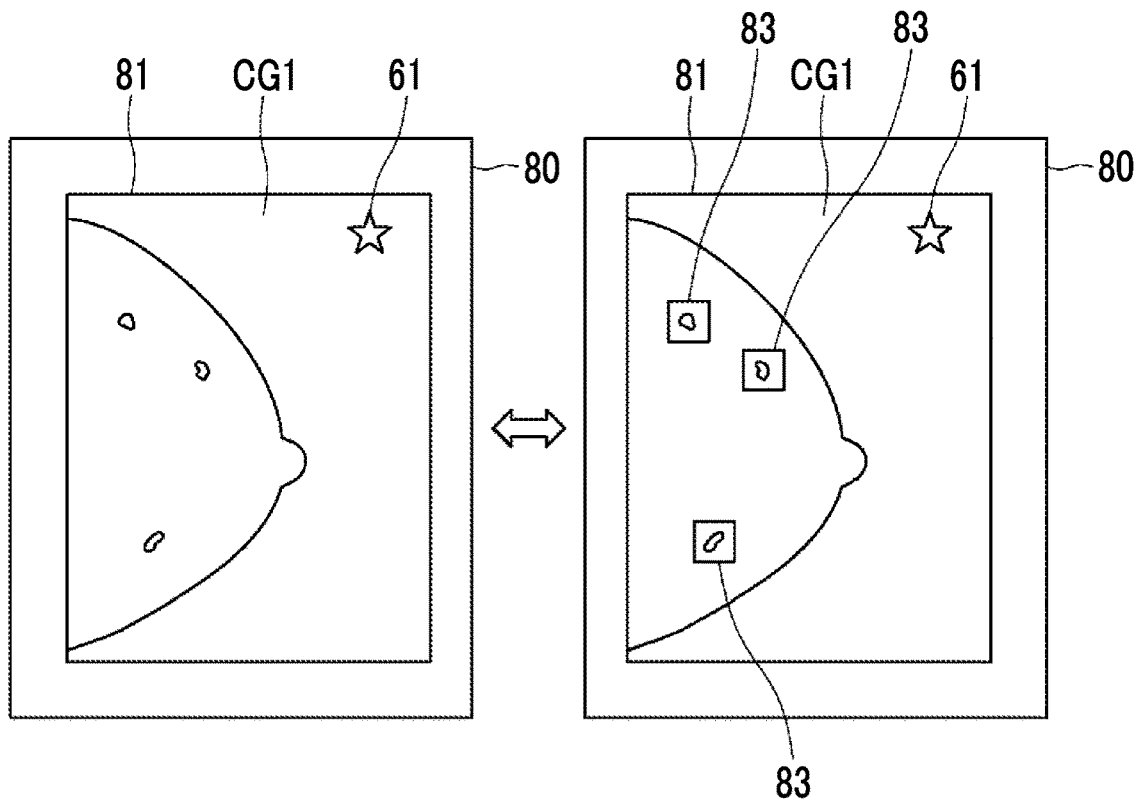
FIG. 14 is a diagram illustrating the switching display of only the different part between the first and second composite two-dimensional images.

In addition, only the first composite two-dimensional image CG1 may be displayed on a display screen 80 and only the different parts between the first composite two-dimensional image CG1 and the second composite two-dimensional image CG2 may be displayed so as to be switched. FIG. 14 is a diagram illustrating the switching display of only the different parts between the first composite two-dimensional image CG1 and the second composite two-dimensional image CG2. The first composite two-dimensional image CG1 is displayed in a display region 81 of the display screen 80 on the left side of FIG. 14. Then, in a case in which the radiologist inputs a display switching command through the input unit 47, only different part regions 83 of the first composite two-dimensional image CG1 from the second composite two-dimensional image CG2 are switched and displayed. As such, in a case in which only the different part regions 83 of the first composite two-dimensional image CG1 from the second composite two-dimensional image CG2 are displayed so as to be switched, it is possible to easily perform comparative image interpretation between the first composite two-dimensional image CG1 and the second composite two-dimensional image CG2.

Figure 15:
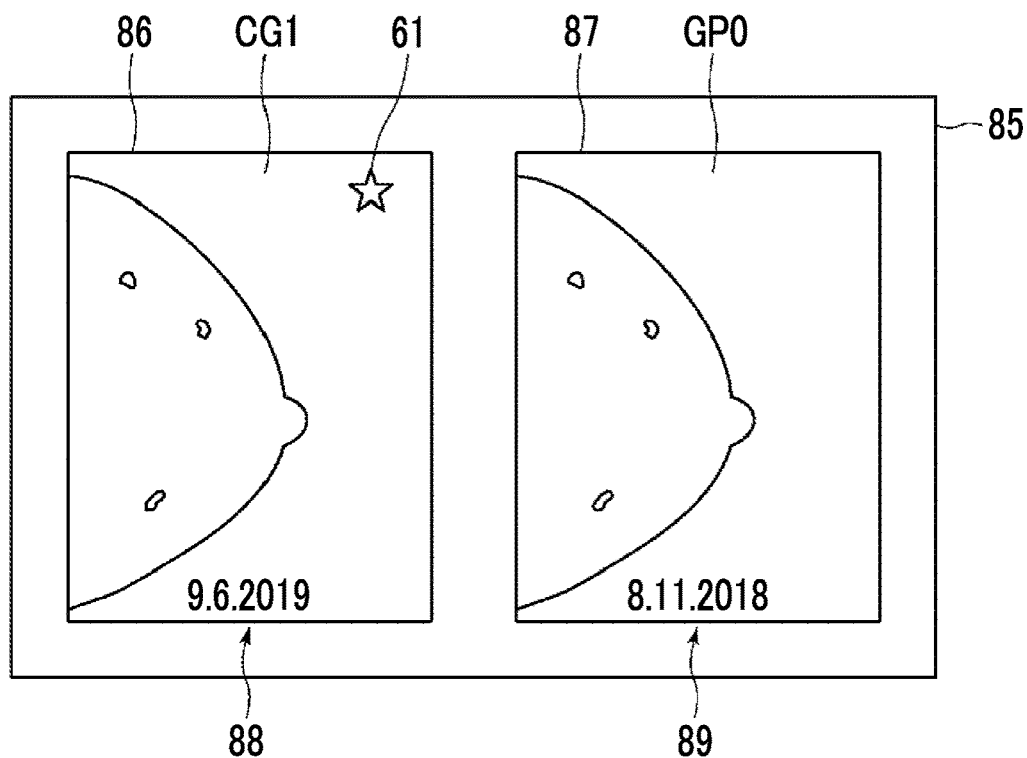
FIG. 15 is a diagram illustrating a display screen for a past radiographic image and the first composite two-dimensional image.

Further, in the above-described embodiment, the image interpretation terminal 8 may display the past radiographic image of the same patient and the first composite two-dimensional image CG1. FIG. 15 is a diagram illustrating a display screen for the past radiographic image and the first composite two-dimensional image CG1. As illustrated in FIG. 15, a display screen 85 includes a first display region 86 and a second display region 87 for displaying the first composite two-dimensional image CG1 and a past radiographic image GPO, respectively. The first composite two-dimensional image CG1 and the past radiographic image GPO are displayed in the first and second display regions 86 and 87, respectively. Therefore, the first composite two-dimensional image CG1 and the past radiographic image GPO are displayed side by side on the display unit 46. The asterisk marker 61 and an imaging date 88 are added to the first composite two-dimensional image CG1 and an imaging date 89 is added to the past radiographic images GPO. The first composite two-dimensional image CG1 has a quality corresponding to the two-dimensional image acquired by simple imaging. Therefore, the side-by-side display of the first composite two-dimensional image CG1 and the past radiographic image GPO makes it possible to easily perform follow-up observation. In particular, in this embodiment, the image quality adjustment unit 34 performs the image quality adjustment process for matching the quality of the past radiographic image of the same patient and the quality of the first composite two-dimensional image CG1. Therefore, it is possible to perform comparative image interpretation between the first composite two-dimensional image CG1 and the past radiographic image GPO without a sense of incongruity.

In FIG. 15, the first composite two-dimensional image CG1 and the past radiographic image GPO are displayed side by side. However, the present disclosure is not limited thereto. The first composite two-dimensional image CG1 and the past radiographic image GPO may be switched and displayed.

Figure 16:
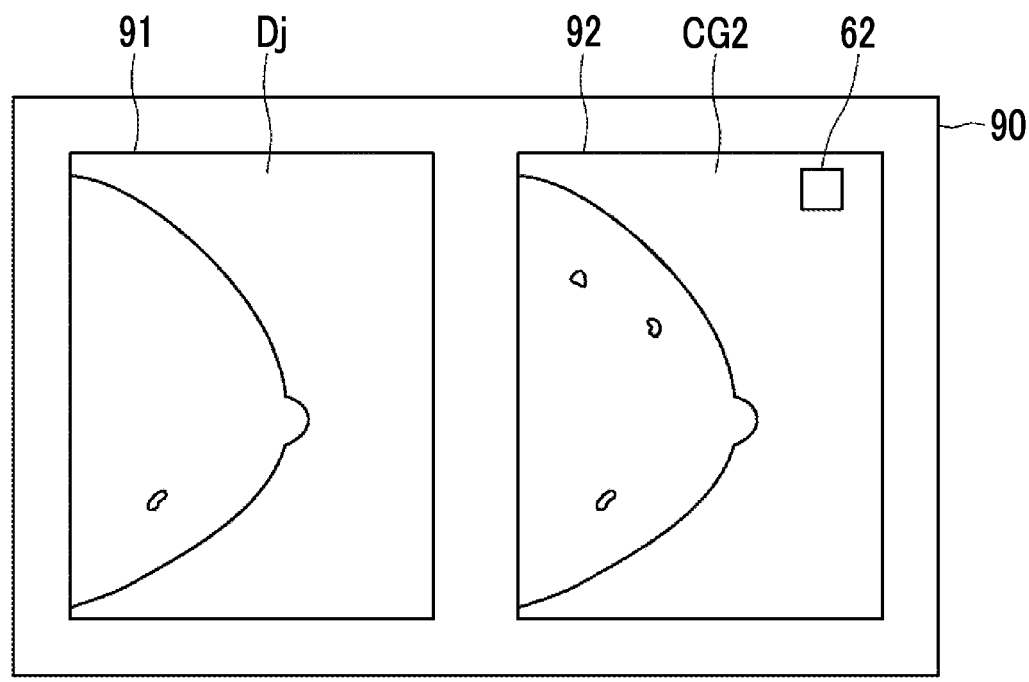
FIG. 16 is a diagram illustrating a display screen for a tomographic image and the second composite two-dimensional image.

Further, in the above-described embodiment, the image interpretation terminal 8 may display a tomographic image and the second composite two-dimensional image CG2 included in an image set. FIG. 16 is a diagram illustrating a display screen for a tomographic image and the second composite two-dimensional image CG2. As illustrated in FIG. 16, a display screen 90 includes a first display region 91 and a second display region 92 for displaying the tomographic image Dj and the second composite two-dimensional image CG2, respectively. The tomographic image Dj and the second composite two-dimensional image CG2 are displayed in the first and second display regions 91 and 92, respectively. Therefore, the tomographic image Dj and the second composite two-dimensional image CG2 are displayed side by side on the display unit 46. In addition, the tomographic plane of the tomographic image Dj can be switched in response to a command from the input unit 47. Therefore, since the tomographic image Dj and the second composite two-dimensional image CG2 are displayed, it is possible to display a tomographic image corresponding to an abnormal shadow included in the second composite two-dimensional image CG2. As a result, it is possible to easily check the abnormal shadow.

The tomographic image and the second composite two-dimensional image CG2 are displayed side by side in FIG. 16. However, the tomographic image and the second composite two-dimensional image CG2 may be displayed so as to be superimposed.

Further, in this embodiment, the image quality adjustment unit 34 may perform an image quality adjustment process for matching the quality of the first composite two-dimensional image CG1 and the quality of the second composite two-dimensional image CG2. In this case, since the quality of the first composite two-dimensional image CG1 is matched with the quality of the second composite two-dimensional image CG2, the radiologist can perform image interpretation using the first and second composite two-dimensional images without a sense of incongruity.

In the above-described embodiment, the image quality adjustment process for matching the quality of the past radiographic image and the quality of at least one of a plurality of composite two-dimensional images is performed. However, the present disclosure is not limited thereto. The image quality adjustment process may not be performed.

In the above-described embodiment, the console 2 performs the combination process, the image quality adjustment process, and the identification information giving process. However, the present disclosure is not limited thereto. The image processing program according to this embodiment may be installed in the image interpretation terminal 8 and the image interpretation terminal 8 may perform the combination process, the image quality adjustment process, and the identification information giving process. In this case, the image set acquired by the image interpretation terminal 8 does not include the composite two-dimensional image. Further, in this case, the CPU 41 of the image interpretation terminal 8 functions as the combination unit 33, the image quality adjustment unit 34, and the identification information giving unit 35.

In a case in which the image processing program according to this embodiment is installed in the image interpretation terminal 8, the combination unit 33 may display the tomographic image Dj on the display unit 46 such that the radiologist selects the structures included in the tomographic image Dj with the input unit 47, instead of detecting structures from the tomographic image Dj using the CAD.

Further, the radiation in the above-described embodiment is not particularly limited. For example, α-rays or γ-rays can be applied in addition to the X-rays.

Further, in the above-described embodiment, for example, the following various processors can be used as the hardware structure of processing units performing various processes, such as the image acquisition unit 31, the reconstruction unit 32, the combination unit 33, the image quality adjustment unit 34, and the identification information giving unit 35 of the console 2 which is the image processing device and the display control unit 51 of the image display device 40. The various processors include, for example, a CPU which is a general-purpose processor executing software (program) to function as various processing units as described above, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

What is claimed is:

1. An image display device comprising a processor, wherein the processor is configured to:
   generate a first composite two-dimensional image from a plurality of tomographic images acquired by performing tomosynthesis imaging on an object and a second composite two-dimensional image in which a structure included in the object has been highlighted from the plurality of tomographic images, wherein the first composite two-dimensional image and the second composite two-dimensional images are generated by different generation methods; and
   display the first composite two-dimensional image and the second composite two-dimensional image so as to be switched.

2. The image display device according to claim 1, wherein the processor is configured to:
   extract a different part between the first composite two-dimensional image and the second composite two-dimensional image, wherein the different part is a region consisting of pixels in which a difference between corresponding pixels of the first composite two-dimensional image and the second composite two-dimensional image is equal to or greater than a predetermined threshold value; and
   display only the different part between the first composite two-dimensional image and the second composite two-dimensional image so as to be switched.

3. The image display device according to claim 1, wherein the processor is further configured to perform a density conversion process and a contrast adjustment process for matching density and contrast of the first composite two-dimensional image and the second composite two-dimensional image.

4. An image display method comprising:
   generating a first composite two-dimensional image from a plurality of tomographic images acquired by performing tomosynthesis imaging on an object and a second composite two-dimensional image in which a structure included in the object has been highlighted from the plurality of tomographic images, wherein the first composite two-dimensional image and the second composite two-dimensional images are generated by different generation methods; and
   displaying the first composite two-dimensional image and the second composite two-dimensional image so as to be switched.

5. A non-transitory computer-readable storage medium that stores an image display program that causes a computer to perform an image display method, the image display program causing the computer to perform:
   generating a first composite two-dimensional image from a plurality of tomographic images acquired by performing tomosynthesis imaging on an object and a second composite two-dimensional image in which a structure included in the object has been highlighted from the plurality of tomographic images, wherein the first composite two-dimensional image and the second composite two-dimensional images are generated by different generation methods; and
   displaying the first composite two-dimensional image and the second composite two-dimensional image so as to be switched.

* * * * *